US009863970B2

(12) United States Patent
Savonsalmi et al.

(10) Patent No.: US 9,863,970 B2
(45) Date of Patent: Jan. 9, 2018

(54) METHOD AND ARRANGEMENT FOR HANDLING TEST TUBES

(71) Applicant: Thermo Fisher Scientific Oy, Vantaa (FI)

(72) Inventors: Juha Savonsalmi, Vantaa (FI); Sami Paavilainen, Vantaa (FI); Ville Mäkelä, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 14/915,911

(22) PCT Filed: Sep. 3, 2014

(86) PCT No.: PCT/FI2014/050674
§ 371 (c)(1),
(2) Date: Mar. 2, 2016

(87) PCT Pub. No.: WO2015/033023
PCT Pub. Date: Mar. 12, 2015

(65) Prior Publication Data
US 2016/0209438 A1    Jul. 21, 2016

(30) Foreign Application Priority Data

Sep. 3, 2013   (FI) ...................................... 20135890

(51) Int. Cl.
*B65G 47/84*     (2006.01)
*G01N 35/04*    (2006.01)
(Continued)

(52) U.S. Cl.
CPC ............. *G01N 35/04* (2013.01); *B65G 29/00* (2013.01); *B65G 47/846* (2013.01);
(Continued)

(58) Field of Classification Search
CPC ........ B65G 17/00; B65G 47/51; B65G 37/00; B65G 47/846; B65G 29/00; B65G 21/2072
(Continued)

(56) References Cited

U.S. PATENT DOCUMENTS 3,941,237 A * 3/1976 MacGregor, Jr. ......... B08B 9/28
                                                                                198/690.1
4,723,661 A    2/1988 Hoppmann et al.
(Continued)

FOREIGN PATENT DOCUMENTS

DE           1084640 B    6/1960
EP           1106542 A1   6/2001
(Continued)

*Primary Examiner* — James R Bidwell
(74) *Attorney, Agent, or Firm* — Seppo Laine Oy

(57) ABSTRACT

A novel solution is proposed for processing a test tube transported on a test tube carrier by a conveyor so that spilling of the liquid in the test tube is reduced or even prevented, particularly an arrangement for sequencing and guiding travel of test tube carriers transported on at least one conveyor. The arrangement includes at least one rotatable deviator positioned to intersect the at least one conveyor. The deviator includes a horizontal deviator plate including at least one grip for receiving a test tube carrier. One contact surface is positioned vertically at a distance from the deviator plate and aligned with the grip. The contact surface is formed to contact the test tube carrier at a distance from the contact level of the grip and the carrier.

19 Claims, 15 Drawing Sheets

(51) Int. Cl.
*B65G 29/00* (2006.01)
*G01N 35/00* (2006.01)

(52) U.S. Cl.
CPC .............. *G01N 35/00732* (2013.01); *B65G 2201/0261* (2013.01); *G01N 2035/00742* (2013.01); *G01N 2035/00782* (2013.01); *G01N 2035/00801* (2013.01); *G01N 2035/0401* (2013.01); *G01N 2035/0467* (2013.01); *G01N 2035/0482* (2013.01)

(58) Field of Classification Search
USPC ........... 198/867.01, 867.11, 867.14, 803.14, 198/480.1, 481.1
See application file for complete search history.

(56) References Cited

U.S. PATENT DOCUMENTS

| | | | | |
|---|---|---|---|---|
| 4,729,413 | A * | 3/1988 | Shults | B65B 43/54 141/18 |
| 5,484,052 | A * | 1/1996 | Pawloski | B65B 43/54 198/803.11 |
| 5,784,857 | A | 7/1998 | Ford et al. | |
| 5,897,090 | A * | 4/1999 | Smith | B01L 9/06 206/306 |
| 5,941,366 | A | 8/1999 | Quinlan et al. | |
| 6,176,369 | B1 * | 1/2001 | Petrovic | B65G 17/002 198/803.14 |
| 6,213,309 | B1 | 4/2001 | Dadisho | |
| 6,343,690 | B1 | 2/2002 | Britton et al. | |
| 6,971,506 | B2 * | 12/2005 | Hassinen | G01N 35/04 198/803.14 |
| 7,858,033 | B2 * | 12/2010 | Itoh | G01N 35/026 422/409 |
| 8,047,359 | B2 * | 11/2011 | Fellows | B65G 17/002 198/803.14 |
| 8,695,791 | B2 * | 4/2014 | Ohman | B65G 47/71 198/803.14 |
| 2002/0081189 | A1 | 6/2002 | Giometti | |
| 2004/0124109 | A1 * | 7/2004 | Hassinen | G01N 35/04 206/443 |
| 2010/0226828 | A1 | 9/2010 | Itoh | |
| 2011/0226584 | A1 | 9/2011 | Ek | |

FOREIGN PATENT DOCUMENTS

| | | |
|---|---|---|
| EP | 2447194 A1 | 5/2012 |
| WO | WO02082095 A1 | 10/2002 |
| WO | WO2011028166 A1 | 3/2011 |
| WO | WO2012071008 A1 | 5/2012 |
| WO | WO2013099647 A1 | 7/2013 |

* cited by examiner

METHOD AND ARRANGEMENT FOR HANDLING TEST TUBES

TECHNICAL FIELD

The present invention concerns an arrangement for transporting test tubes automatically between various process stages, analyzers and other equipment in laboratories.

Especially the invention concerns arrangements for transporting test tubes on a conveyor and picking them from the conveyor and loading then back on a conveyor.

BACKGROUND

In analysis laboratories, it is necessary to handle large number of samples and to transport them between different process stages and analyzers. The samples are placed in test tubes, which are loaded into and removed from apparatuses such as centrifuges and analyzers. The transport and handling of test tubes may be carried out manually, but various automatic handling systems are increasing in laboratories, due to the increase in the number of samples and the efficiency of analysers. The basic requirements for an automatic conveyor system are the reliable and undamaged handling of test-tubes and the reliable monitoring of the samples in the system. Reliable handling is usually implemented by placing the test tube in a separate transport base, which is guided as it is moved by a conveyor belt along a mechanically delimited track. The position of the test tubes within the system is monitored with the aid of barcodes and code readers and RF chips.

Publication U.S. Pat. No. 5,605,218 discloses a conveyor track, in which the transport base is moved in a U-shaped groove with conveyor bands running in its corners. The bands have a circular cross-section and are arranged to run as parallel continuous loops. Canadian patent application 2,216,052 discloses a system for handling test tubes containing biosamples. In this solution, there are at least two transportation lanes, along which the test tubes, located in transport bases, are moved. EP 0 633 207 discloses a transport system wherein samples are picked from a track with robot arms and transferred to further handling.

Further examples of laboratory automation equipment are described in GB 2 189 884, EP 0 856 736, U.S. Pat. No. 5,370,215, U.S. Pat. No. 5,941,366 and U.S. Pat. No. 5,658,532. Documents EP 0 916 952, DE 43 29 078 and DE 26 44 137 disclose test tube handling methods utilizing rotary deviators.

As the demands for increasing throughput of laboratories increase, demands for increasing transfer speed of the test tubes on the conveyors as well as handling times at various handling stations, are increased. On particular problem in increasing transfer speed or decreasing the cycle time is that acceleration and deceleration of the test tubes becomes harsher. Since liquids in the test tubes move freely and the tubes are often open, acceleration and deceleration as well as tilting or rocking of the test tubes should be controlled so that no spilling of the liquid occurs. Further aspects that are relevant are efficient and reliable detection of test tubes or test tube holders incoming and leaving the handling stations or deviators. One useful aspect would be to decrease the need for stopping the holders and test tubes as then the deceleration and acceleration are greatest.

For the above reasons, it would be beneficial to provide an arrangement and method that provides means for removing a carrier from a deviator to a conveyor without stopping the movement of the carrier.

Further, it would be beneficial to provide a deviator that could process a test tube transported on a test tube carrier by a conveyor so that spilling of the liquid in the test tube is reduced or even prevented.

In a first aspect, the invention relates to a method and apparatus for deviating a test tube transported on a carrier away from the direction of the travel of a conveyor.

According to one aspect of the invention, the invention provides means for force feeding test tube carriers from the deviator to a conveyor.

One embodiment of the invention relates to receiving a carrier with a test tube on a deviator in a manner wherein tilting of the carrier and the tube thereon is reduced or prevented.

According to one further aspect of the invention, the invention provides a method and means for sequencing the test tube carriers coming to a deviator in an efficient manner.

The invention is based on a rotatable deviator that comprises a horizontal deviator plate comprising at least one grip for receiving a test tube carrier and a push plate positioned in proximity of the deviator plate and having at least one pushing surface formed as an arc that starts as a tangent of a circle that the bottom of the recess of the grip travels and then curves outwards from said circle.

According to one embodiment of the invention, at least one push plate is positioned in proximity of the deviator plates of at least two deviators and having four pushing surfaces formed as an arc that starts as a tangent of a circle defined by the track that the bottom of the recess of the grip (21) travels and then curves outwards from said circle.

According to one embodiment of the invention, the deviator comprises at least one contact surface at a distance from the deviator plate and aligned with the grip, the contact surface being formed to contact the test tube carrier at a distance from the contact level of the grip and the carrier.

According to one embodiment, at least the grip is a recess on a circular plate.

According to one embodiment, the contact surface is a recess on a circular plate.

According to one embodiment of the invention, the grip and the contact surface are formed as a part of an arc of a circle.

According to one embodiment of the invention, at least one of the recess of the contact surface or the recess of the grip is an elongated slot.

According to one embodiment of the invention, the grip and the contact surface are formed as a part of an arc of a circle.

According to one embodiment of the invention, the deviator comprises at least two grips and contact surfaces.

According to one embodiment of the invention, the deviator comprises four grips and contact surfaces.

According to one embodiment of the invention the test tube carrier comprises a circular glide plate having a diameter and a thickness, a neck part having preferably a circular cross section, on top of the glide plate, having a length and a diameter smaller than the glide plate and a meshing plate having a diameter and a thickness and being placed at a distance from the glide plate.

According to one embodiment the glide plate comprises a RFID chip and the diameter of the neck part is smaller than the largest diameter of the chip.

According to one embodiment, the carrier comprises a detection surface positioned between the neck part and the meshing plate, the detection surface having a thickness and a diameter smaller than the diameter of the meshing plate and larger than the neck part.

According to one embodiment, the glide plate comprises a seat for a RFID chip to which the chip can be installed from the bottom surface of the glide plate opposite to the neck part so that the chip can be read from the bottom of the carrier formed by the bottom surface of the glide plate.

The invention provides several benefits.

One of the essential benefits of the invention is the possibility to shorten cycle times in various stages of test tube handling, especially at deviators. The test tube carries can be taken to the deviator at greater speed and pushed actively on a conveyor without stopping the movement of the test tube carrier, whereby cycle times can be greatly shortened.

Another beneficial feature is better control of liquid in test tubes, essentially in long and high test tubes. The splashing and spilling of liquid is reduced or avoided. This is important in laboratories where fluid samples of biological origin are handled and danger of contamination is present.

The conveyor system can be easily modified to accommodate various track designs and routes. The system can be built as modules that can be combined together in order to provide a desired automation system for customer's needs. Conveyors, tracks and deviators can be assembled on a simple base plate as a layer structure that provides easy assembly and modifiability.

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

DESCRIPTION OF EMBODIMENTS

Definitions

Figure 1:
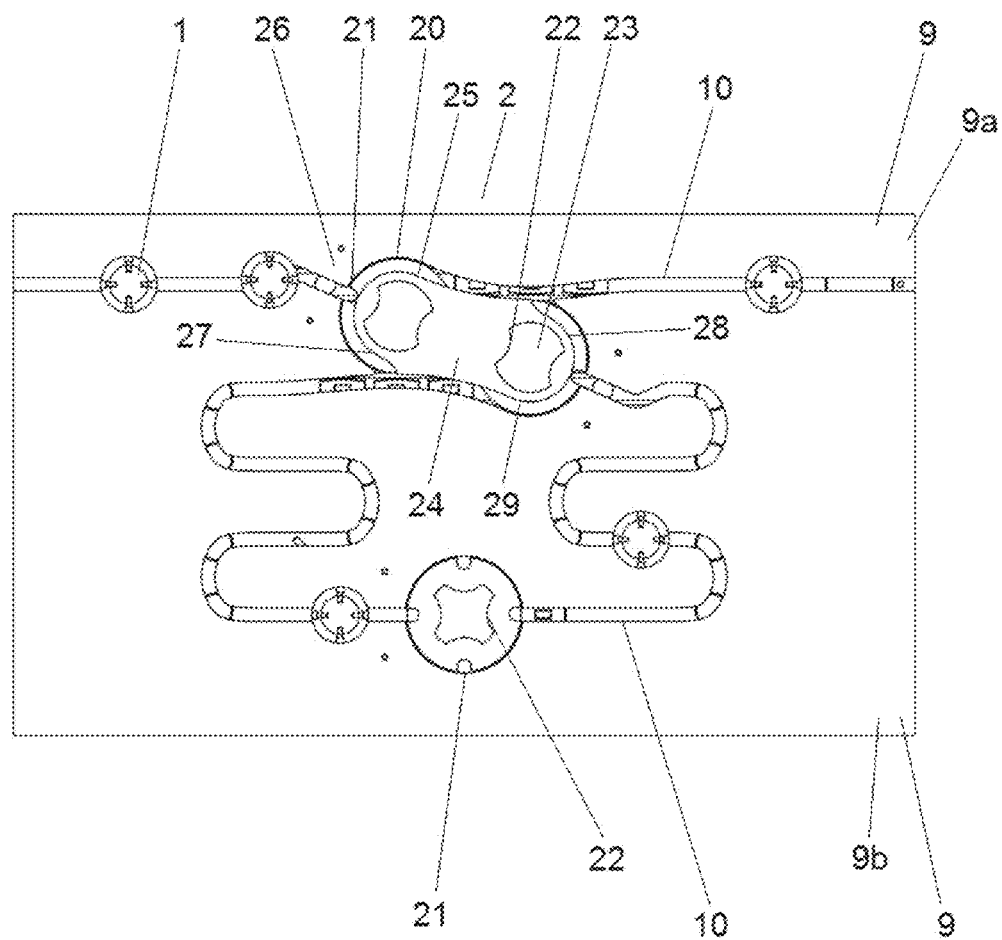
FIG. 1 is a top view of one embodiment of the invention.
Figure 2:
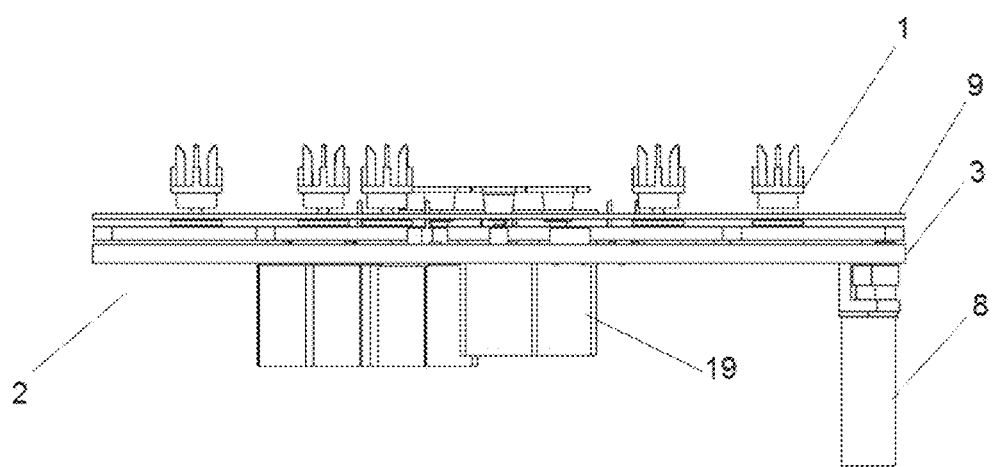
FIGS. 2-4 are side views of the embodiment of FIG. 1.
Figure 3:
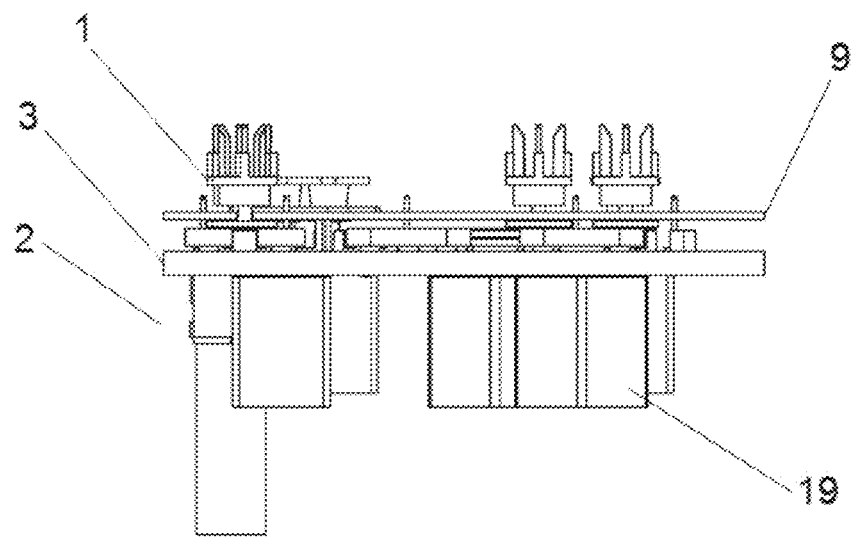
Figure 4:
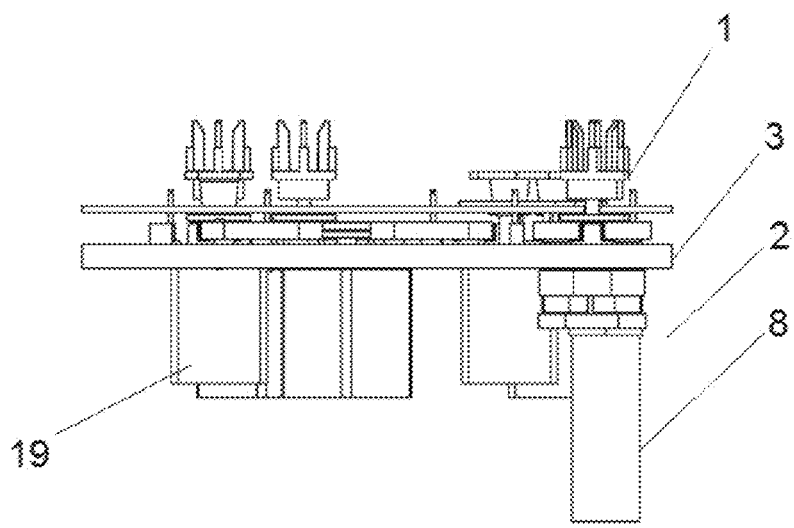
Figure 5:
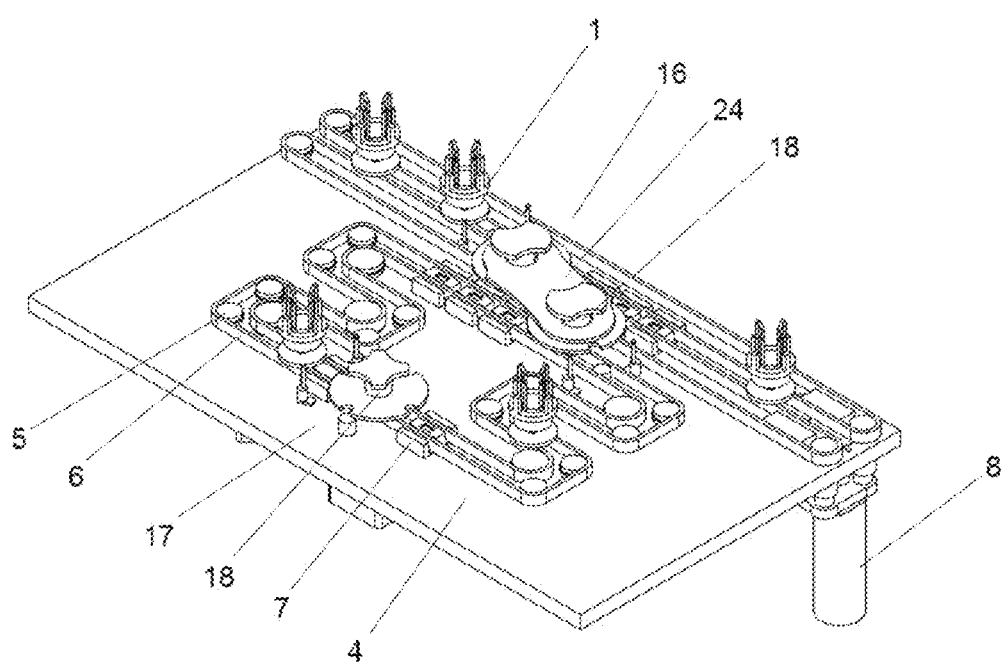
FIG. 5 depicts embodiment of FIG. 1 without a top guide plate.

A test tube is any vessel capable of carrying liquid, in practice a longitudinal test tube used conventionally in laboratories.

A test tube carrier is a holder on which a test tube can be mounted for transportation on a conveyor.

A conveyor is a transportation system for moving test tube carriers on a predetermined path.

FIGS. 1-6 depict one embodiment of the invention. This embodiment is a module for transporting and handling test tubes placed on carriers. For simplicity, in the following it is referred only to carriers without mentioning the test tubes. The transportation module 2 is built on a base plate 3. The base plate 3 is a simple flat plate made of sufficiently rigid material and comprising mounting places for parts of the module 2. On top of the base plate 3 is mounted conveyors 4, that comprise guide wheels 5 and conveyor belts 6 arranged to travel in an upright position so that the edge of the belt 6 forms a support surface of the conveyor 4. The edges of the belts 6 carry and transport the carriers 1. This type of a conveyor is described in U.S. Pat. No. 6,520,313. The track of each conveyor 4 is set by guide wheels 5 that are placed on turning points of the belts 6. Each conveyor comprises two belts 6 that are arranged to travel parallel to each other at the area of a guided track. The belts 6 are further guided and supported by guide blocks 7 that keep the belts 6 on upright position. The guide blocks 7 and guide wheels are arranged at a distance from each other. In this way dust or other impurities don't aggregate easily in gaps between the guiding elements, whereby cleaning and maintenance is easy. The module 2 in FIGS. 1-6 comprises two conveyors 4, one travelling along a long straight edge of the base plate 3 and forming a straight path of travel. The other conveyor 4 forms a convoluting loop on the side of the straight conveyor. The belts 6 of the conveyors 4 are operated by drive motors 8 positioned on the underside (opposite to the conveyors) of the base plate 3.

The conveyors 4 and other parts mounted on the base plate are covered by a guide plate 9 mounted on a distance from the base plate 3. The guide plate 9 comprises at least one groove 10 for forming a guided track over the conveyors 4 along which the carriers 1 are set to travel. The groove 10 can be cut on the guide plate 9 or the guide plate can be formed of separate pieces 9a, 9b so that the edge of the pieces form the groove or grooves 10 for guiding the carriers 1 over the conveyors 4.

The distance between the base plate 3 and the guide plate 9 is set such that carriers 1 can be set to travel on top of the conveyor belts 6 guided by the grooves 10. This dimensioning depends on structure and dimensioning of the carriers 1. The carriers used in this invention are rotationally symmetric and formed like stem glass. The carrier 1 comprises a circular glide plate 11 having a diameter and a thickness, a neck part 12 on top of the glide plate 11, having a length and a diameter smaller than the glide plate 11 and a meshing plate 13 having a diameter and a thickness and being placed at a distance from the glide plate 11. The distance between the bottom of the glide plate 11 and the top of the meshing plate 13 determine the height of the body of the carrier 1. On top of the meshing plate are arranged holders 15 for test tubes. The structure of the holders does not belong to the scope of the invention and is therefore not described herein.

The glide plate 11 comprises seat for a RFID chip that can be placed within the glide plate 11 from the bottom of the glide plate 11. This way of mounting the chip provides reliable reading of the chip under the carrier 1. Further, the neck part 12 of the carrier can be made very thin as it is not necessary to place the chip to the glide plate 11 through the neck part 12. In this way the diameter of the neck part 12 can be made smaller than the largest diameter of the chip. The diameter of the neck part 12 is very important regarding the operation speed and cycle times of the deviators. A thin neck part needs a shorter transfer distance when pushed into the grip of a deviator. Shorter transfer distance means naturally shorter transfer times. Basically the neck may be made as thin as possible. The diameter of the neck part is limited by the required constructional strength. The neck part 12 must be rigid enough to withstand stresses of handling and transportation without deformation or damage and it may not bend or cause vibration of the carrier in use. The diameter of the neck part 12 should be noticeably smaller than the diameter of the glide plate 11. The diameter of the neck part is 70% of the diameter of the glide plate at most in order to obtain reasonable benefit of the narrowed neck part. However the diameter of the neck part should be preferably 50% or most preferably 30% of the diameter or the glide plate in order to improve more the cycle times and operational speed of the system. Since the neck part is preferably quite thin, the recess in the carrier made for receiving a test tube doesn't penetrate on the neck part and is set above the top of the neck part.

The carrier comprises also a detection surface 14 positioned between the neck part 12 and the meshing plate 13, the detection surface 14 having a thickness and a diameter smaller than the diameter of the meshing plate 13 and larger than the neck part 12. The purposes and benefits of this design will be made apparent in following. As the glide plate 11 comprises a seat for a RFID chip to which the chip can be installed from the bottom surface of the glide plate 11 opposite to the neck part 11, the chip can be read from the bottom of the carrier formed by the bottom surface of the glide plate.

Figure 6:
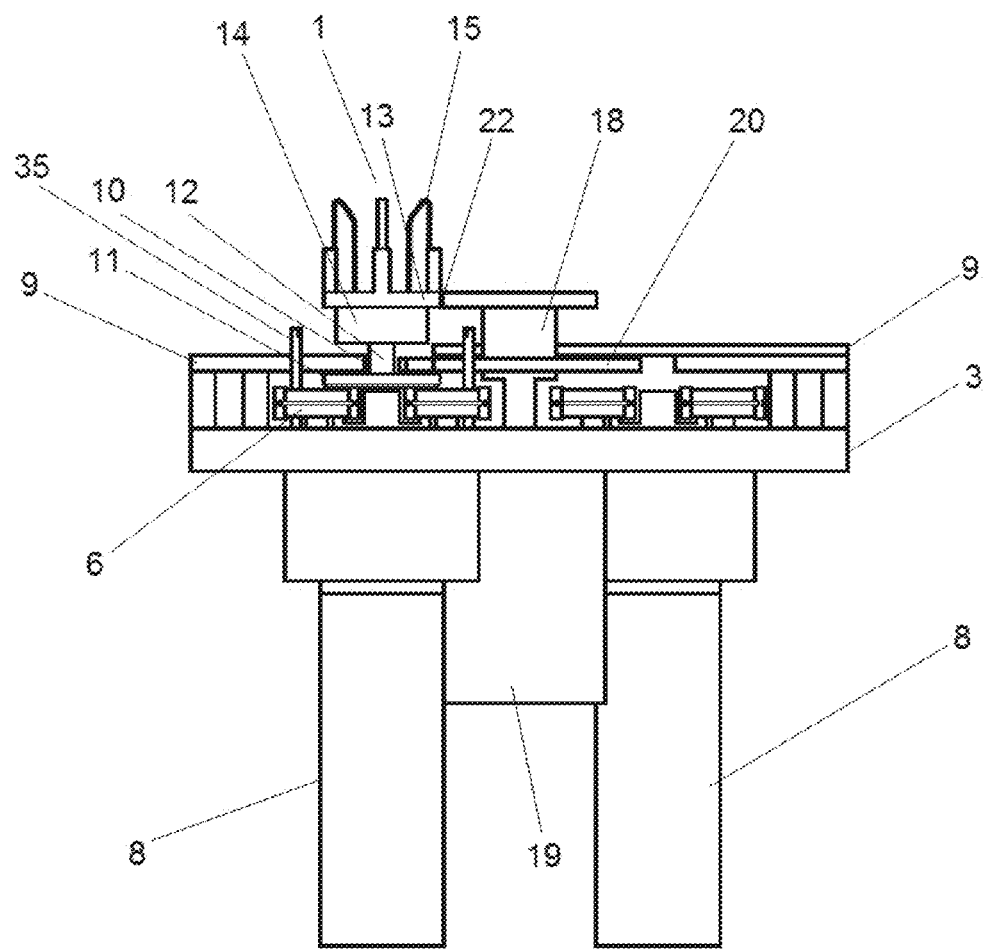
FIG. 6 is a schematic side view of the embodiment of FIG. 1.

Some reasons for the above described design can be seen from FIG. 6. The thickness of the glide plate 11 is dimensioned so that the glide plate 11 fits between the tops of the conveyor belts 6 and the underside of the guide plate 9. On the other hand, the distance between the top of the base plate 3 and the underside of the guide plate is set such that there is enough room for the guide plate 11 to travel between the tops of the belts 6 and the underside of the guide plate 9. The width of the groove 10 is slightly wider than the diameter of the neck part 12 of the carrier 1. Sufficient play between these parts is needed in order to provide smooth travel of the carriers 1 on top of the belts 6. However, this play allows the carrier to tilt slightly. This causes problems during any kind of acceleration as the test tubes are tilted accordingly and the liquid placed in a test tube carried on the carrier moves in the tube. Also any acceleration even without tilting causes the liquid to move within the test tube. This may cause splashing of the liquid. In a laboratory environment splashing can't be tolerated as any spilling of liquid may cause dangerous or harmful contamination.

One way to control tilting and accelerations of carriers and test tubes is to use a deviator 16, 17 according to the invention. The deviator is best illustrated in FIG. 5 and FIGS. 23A-C. The purpose of deviators 16, 17 is to sequence and guide the travel of carriers. Deviators are rotatable bodies that comprise a stem 18. The stem 18 is mounted on the base plate 3 and is connected through the base plate 3 to an electric motor 19, a deviator motor for rotating the deviator. The motor is a step motor or other motor that can be driven controllably and preferably on two directions at controlled speed and to accurate positions. On the stem 18 is mounted a horizontal deviator plate 20 comprising at least one grip 21 for receiving a test tube carrier 1 and at least one contact surface 22 mounted on the stem 18 at a distance from the deviator plate 20 and aligned vertically with the grip 21, the contact surface 22 being formed to contact the test tube carrier 1 at a distance for the contact level of the grip 21 and the carrier 1. In this embodiment the contact surface 22 is formed on a horizontal circular bumper plate 23 by forming cuts therein that mesh with the form of the meshing surface 13 of the carrier 1.

In this embodiment, the grip 21 is a recess on a circular plate and the contact surface 22 is also a recess on a circular plate. The grip 21 and the contact surface 22 are formed as a part of an arc of a circle. In this way they match and mesh well to rotationally symmetric form of the carrier. Optionally, according to one embodiment of the invention, at least one of the recess of the contact surface 22 or the recess of the grip 21 is an elongated slot formed on the edge of a circular plate. In this way positioning of the deviator does not have to be accurate when receiving the carriers and the deviator may operate on shorter cycle times. The recesses may also comprise holders to ensure gripping of the carrier or cushioning material for dampening the contact between the deviator and the carrier. The recess may also be formed to form a releasable locking contact with the carrier.

The grip 21 and the contact surface 22 may be formed as a part of an arc of a circle. If the recess is an elongated slot extending along the perimeter of a circular plate, the ends of the slot may be made circular to match the diameter of the carrier or may have horns or points extending towards the slot in order to guide and hold the carrier.

Figure 23A:
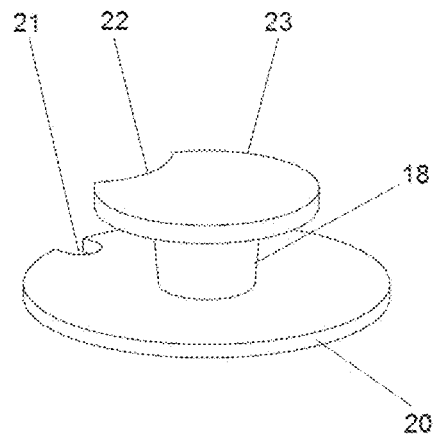
FIGS. 23A-D show four embodiments of a deviator.
Figure 23B:
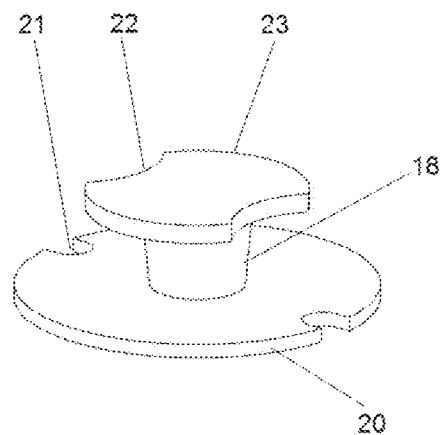
Figure 23C:
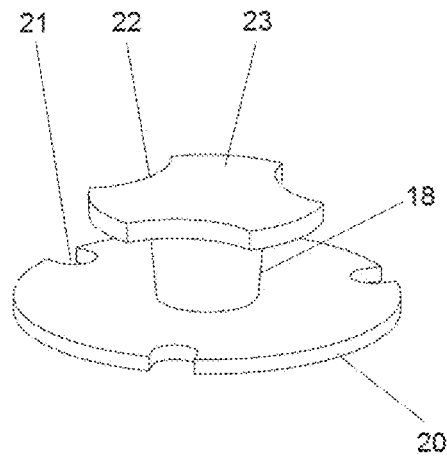
Figure 23D:
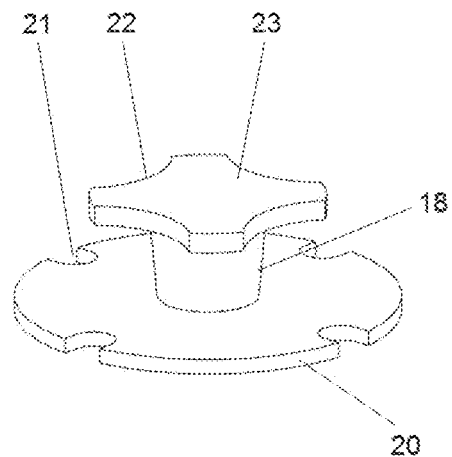

Usually the deviator comprises an even number of grips 21 and matching contact surfaces. The embodiments shown in drawings 1-22 comprise four grips and contact surfaces or two grips and contact surfaces. FIGS. 23A and 23B show a deviator with one grip and contact surface and a deviator with three grips and contact surfaces. The most advantageous number of grips and contact surfaces is dependent on how many conveyor tracks are used and the lay-out how they are arranged in relation to each other. For example, if number of receiving and exit positions is three or six, a deviator with three grips (FIG. 23C) might be most useful.

As described above, the grips and contact surfaces may take many alternative shapes. Regardless of how they are formed or shaped, these surfaces should match the surfaces of the carrier so that the carrier contacts the surface of the grip and the contact surface simultaneously when the carrier enters the deviator.

The deviator plate is arranged on same or approximately same level as the guide plate 9 in such a way that carriers 1 guided by the groove 10 can be caught by the grip 21. In order to be able to do this, the deviator plate has to be positioned so that it is on the level of the neck part 12 of a carrier 1 travelling on the belts 6. When a carrier enters incoming zone of a deviator 16, 17, it is caught at its neck part 12 by the grip 21. Now the carrier can be turned (deviated) to either way from the catching point in order to place it on a different conveyor, further on a same conveyor or to an analyzer or to another laboratory equipment.

One feature that enhances the functionality and reliability of the invention and enables to shorten cycle times is a push plate 24 positioned in proximity of the deviator plate 20 and having at least one pushing surface 25 formed as an arc that starts as a tangent of a circle defined by the track that the bottom of the recess of the grip 21 travels and then curves outwards from said circle. The pushing surface is positioned to begin at the exit of a deviator 16 and its function is to guide the carrier to next conveyor. As can be seen from FIG. 1, the push plate 24—as the pushing surface 25 begins tangentially at the turning radius of the grip and a carrier placed therein—pushes the carrier gently forward towards the next conveyor, which in this embodiment is physically the same as the incoming conveyor, the track of which extends on the exit side of the deviator. In the embodiment of FIG. 1, the push plate 24 has several pushing surfaces 25, 27-29, namely one 25 set clockwise from the incoming zone of a deviator 16 that guides the carrier to further on the same conveyor it has been travelling and one set counterclockwise from the incoming zone 26 to push a carrier to a parallel conveyor. As this embodiment comprises two parallel deviators 16, they share a common push plate 24. Pushing surfaces 28 and 29 are used to push carriers from the other deviator to either of the conveyors. The number of deviators and push plates and pushing surfaces may be varied and combined according to the number of exit and income positions needed. For example, one deviator and one push plate may be used. The push plate can be formed of more than one part.

Figure 7:
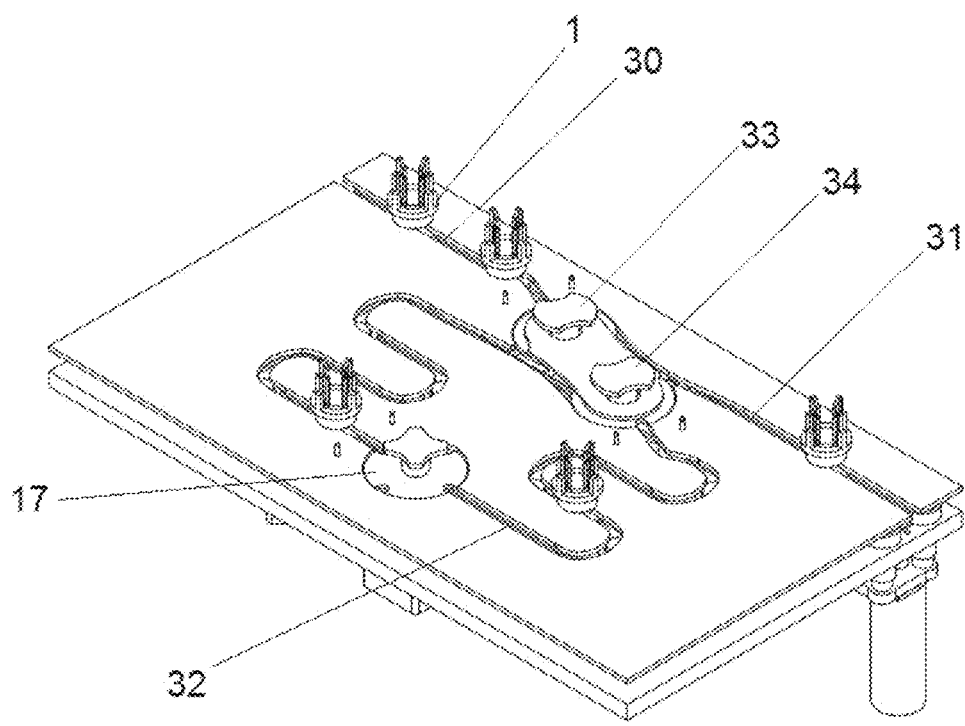
FIG. 7 shows an embodiment of a track arrangement according to the invention.

FIG. 7 shows an example of a transport and handling module for test tubes. This embodiment comprises two conveyors, a straight conveyor having an incoming side 30 leading to a pair of deviators 33, 34, and an exit side 31 extending from the pair of deviators 33, 34. The convoluting conveyor 32 is arranged to adjoin the pair of deviators 33, 34 and forms a serpentine track for the test tube carriers 1. The convoluting conveyor 32 intersects a four-grip deviator 17. The conveyors shown herein are examples only and the tracks can be modified according to need of the user. This assembly can be used for example as a buffer track or for transferring test tubes to an analyzer and for changing the order of the test tubes. The pair of deviators 33, 34 can be used for forwarding the test tubes from incoming side 30 of the track to the exit side 31 or for feeding the test tubes to and from the convoluting tack 32. The convoluting track 32 can be used as a buffer wherein the test tubes are stored for a while before they are forwarded further in the system. The four-grip deviator 17 is well suitable for feeding test tubes to and from an analyzer or other apparatus.

Figure 8:
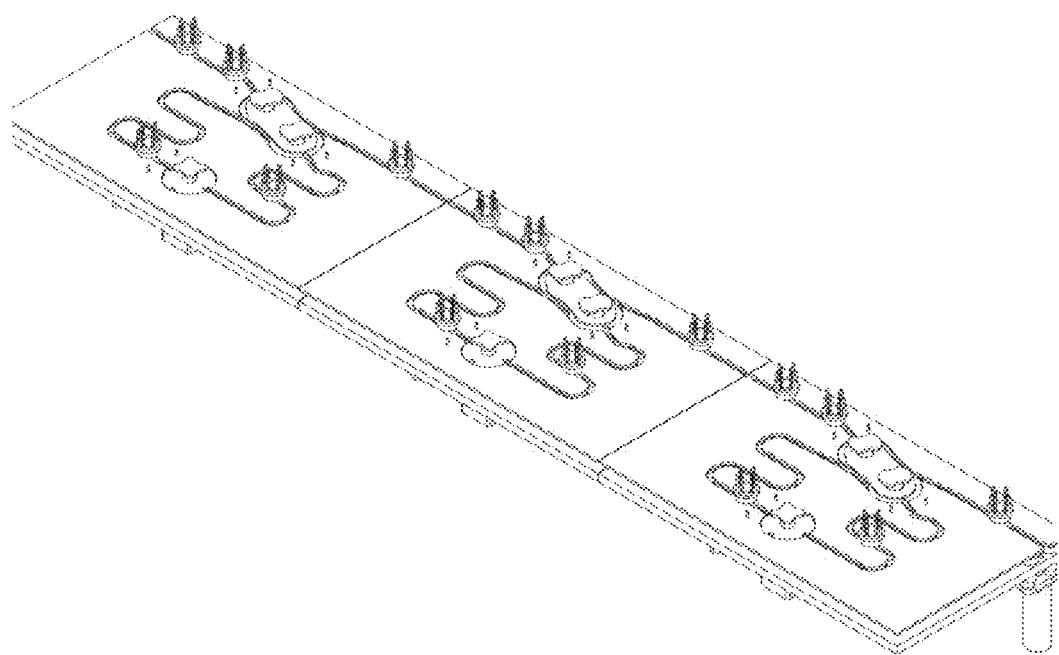
FIG. 8 shows another embodiment of a track arrangement according to the invention.

The modules described in FIG. 7 may comprise all necessary elements for operation of the module. Therefore the modules can be used independently or combined to a track system. One example of such a track system is shown in FIG. 8, wherein three modules are combined successively. In this example all modules are similar, but as mentioned earlier, the tracks and the number of the deviators may be altered.

Figure 9:
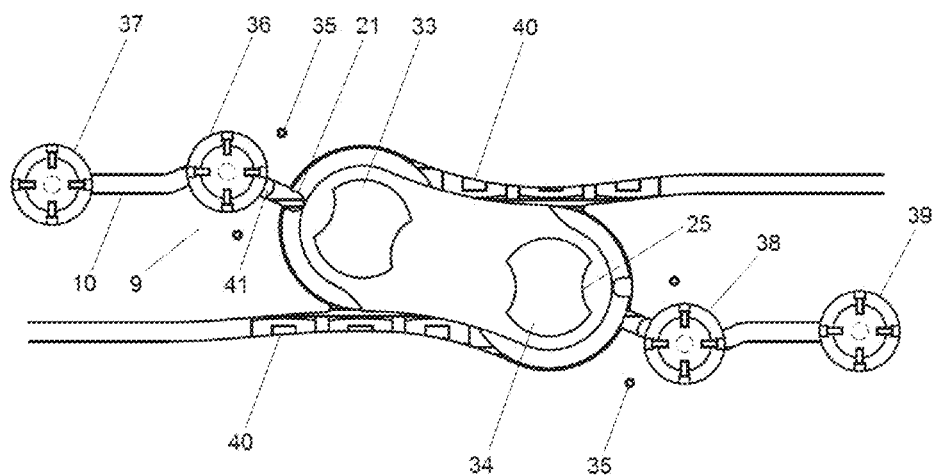
FIGS. 9-15 depict sequences for guiding the test tube carriers through a pair of deviators.

Various operations may be performed in order to change the track or order of the test tubes. These possibilities are explained further referring to the FIGS. 9-15 and 16-21. The set of FIGS. 9-15 shows examples of handling operations using a pair of deviators operating together. In FIG. 9, first deviator 33 is in a position wherein a grip 21 and pushing surface 22 are aligned with the incoming groove 10 of the conveyor 4. First and second test tube carriers 36, 37 are approaching the deviator 33 on the incoming side 30 of the conveyor. On the incoming side 30 of the conveyor is a photodetector that uses a light beam for detection of the presence of a test tube carrier 36. Since the grip 21 is aligned with the groove of the guide plate 9, the carrier 36 may enter the grip 21 and is held by it. Simultaneously the meshing plate 13 contacts with contact surface 22 of the bumper plate 23 of the deviator 33 preventing tilting of the carrier and the test tube (not shown) carried by it. The carrier is now supported by the neck part 12 and the meshing plate 13 of the test tube carrier. The detection surface 14 of the test tube carrier 36 (see FIG. 6, ref. 1 also) intersects the beam of the photodetector 35 when it passes the photodetector 35 and when the carrier 36 has entered the grip 21, the detection surface does not block the beam of the detector 35. Now the photodetector 35 indicates that the carrier 36 has entered the first deviator 33 and the first deviator 33 can be turned. As the photodetector 35 indicated arrival of a carrier it also triggers reading sequence of a RFID-reader 41 placed under the groove 10 of the conveyor. Now the deviator recognizes the carrier and knows where it should be guided.

Figure 11:
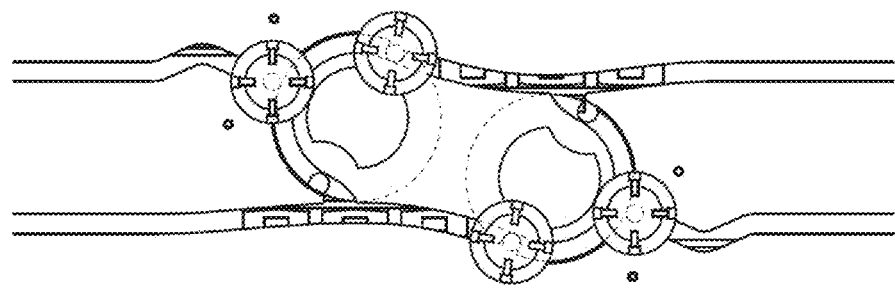
Figure 12:
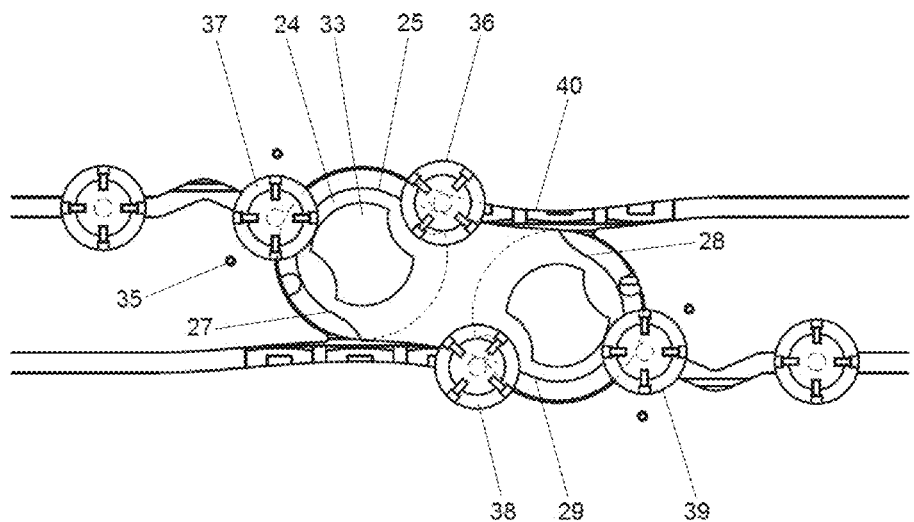

The dimensioning of the test tube carrier 1 plays an important role in the controlling the movements of the deviators and test tubes. As can be seen in FIG. 6, the narrowest part of the carrier 1 is the neck part 12 and the glide plate 10 and the meshing plate 13 have the largest diameters. The diameter of the detection surface 14 is smaller than the diameter of the meshing plate 13. This dimensioning is used for following reason. When the first test tube carrier 36 enters the grip 21, the beam of the photodetector 35 passes the detection surface 14 as its diameter is smaller than the diameter of the meshing surface 13 resting on the bumper plate 23. In this stage the RFID of the test tube carrier 36 has been read and entering of it to the first deviator 33 indicated. If the first deviator 33 is not turned, the second test tube carrier 37 comes into contact with the first carrier 36 so that the meshing surfaces 13 of the successive carriers contact each other. This leaves a gap between the detection surfaces 14 of the first and second carrier 36, 37. Now the second test tube carrier 37 does not trigger the photodetector and RFID of the second test tube carrier is not read. This prevents reading of further RFID information before previous test tube carrier has been transferred. This feature is need to guarantee that the deviators always have information of which carrier is being handled. When the first test tube carrier 36 is turned away from the receiving position, in this case to the exit part 31 of the conveyor as shown in FIG. 11, the second test tube carrier 37 is pushed forward and the neck part 12 of it contacts the outer surface of the deviator plate 20 and outer surface of the bumper plate 23 of the first deviator 33. Now the beam of the photodetector 35 is intersected again and RFID of the second test tube carrier 37 is read. In this position the detecting surface intersects the beam of the photodetector continuously until the first deviator 33 is turned and the carrier 37 pushed to the grip 21.

When the first deviator 33 is turned, it is guided by the pushing surface 25 of the pushing plate 24. The pushing surface is formed as an arc that starts as a tangent of a circle defined by the track that the bottom of the recess of the grip 21 travels and then curves outwards from said circle. In this way the pushing surface guides the test tube carrier gently to the exit side of the straight conveyor 31. When the carrier 36 is pushed on the belts 6 of the conveyor, the belts rapidly pick up the carrier 36 and transfer it along the groove 10 forward away from the first deviator 33. The exit side of the straight conveyor 31 comprises three detectors for sensing a presence of a carrier. The detectors are placed under the level of the top of the belts 6 so that a carrier placed upon belts is set over at least two detectors 40. The detectors 40 cover the exit sides of both deviators 33, 34 at exit side of the straight conveyors as well as the convoluted conveyor 30. The purpose of these detectors is to secure that the exit side is free from carriers before either of the deviators 33, 34 feed further carriers on the exit zone.

The second deviator 34 operates basically in a similar manner as the first deviator 33 described above. Both deviators can be turned either way and they receive carriers from one incoming track and can release them to two different tracks. The tracks of the conveyors and positioning of the deviators shown herein include some examples of various possibilities to implement the invention. In the following some of the many possible carrier guiding sequences are described as an example.

Figure 10:
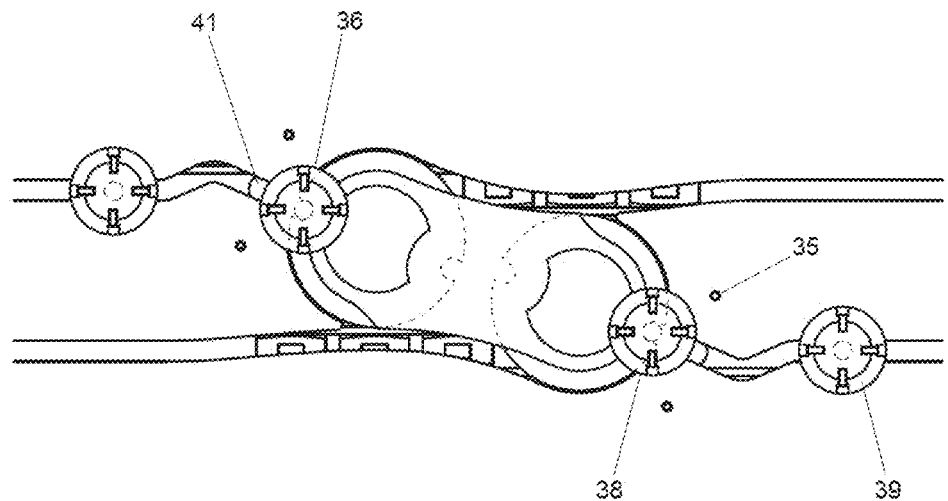

In FIG. 9 third and fourth test tube carriers are entering the second deviator 34, that is positioned as the first deviator 33 in between two conveyors so that the grips 21 of the deviator can be rotated on both of the conveyors. In FIG. 9, first deviator 33 is ready to receive a carrier. The second deviator is in rotational position wherein the outer surface of the deviator plate closes the entrance to the deviator, whereby the third test tube carrier 38 would be stopped by that surface. In FIG. 10 the second deviator is turned so that the third carrier can be received by the grip 21 and both deviators hold a carrier. In next stage deviators 33, 34 have turned the first and second carrier 33, 38 almost to the exit on a next position on the track. Entrance of second and fourth carrier is blocked and first and third carriers are released. In this sequence the carriers continue on the same conveyor.

Figure 13:
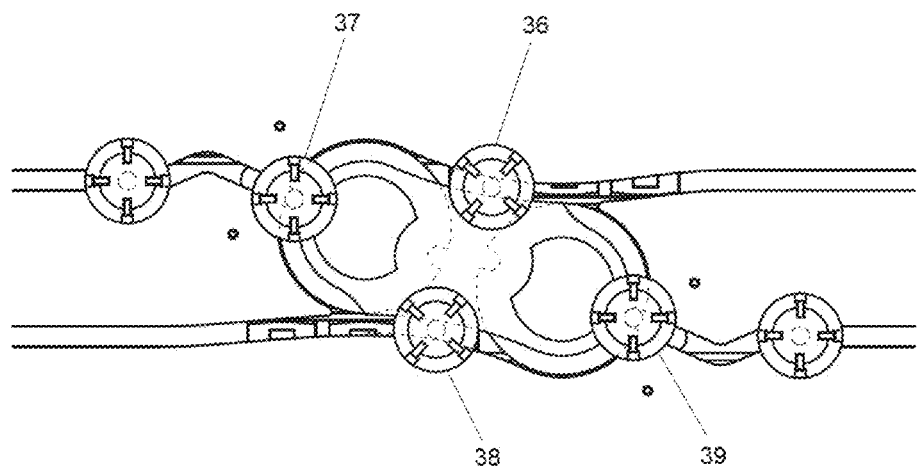
Figure 14:
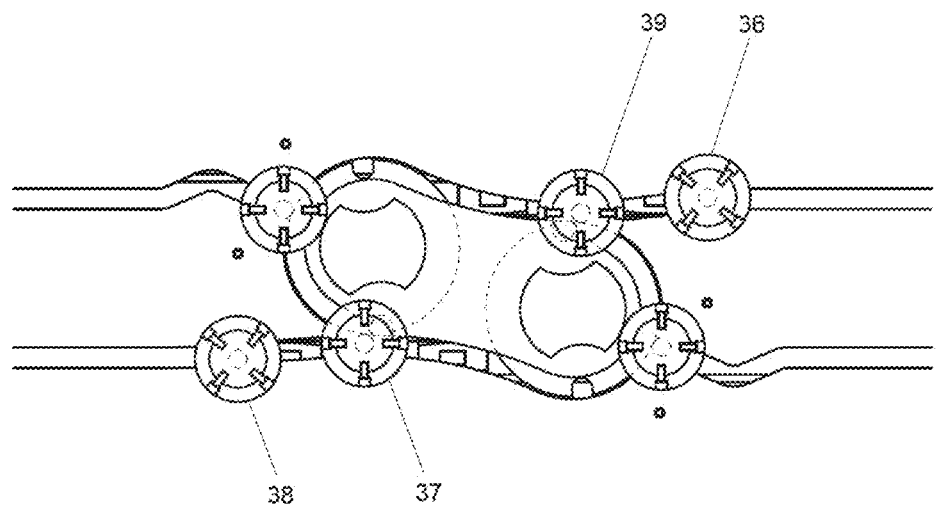
Figure 15:
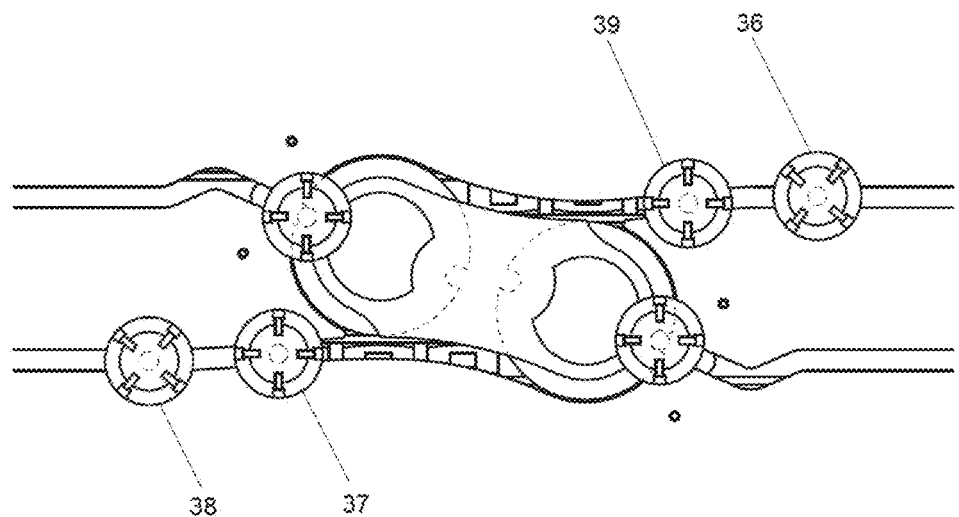
Figure 16:
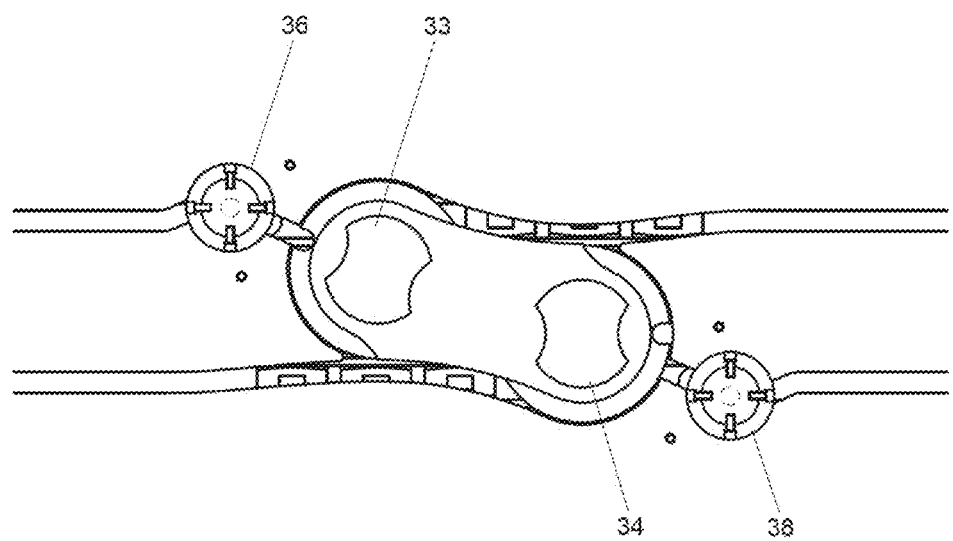
FIGS. 16-22 show further sequences for guiding the test tube carriers through a pair of deviators.

In FIG. 13 first 36 and third carrier 38 are fully released and placed on top of detectors 41 arranged at the conveyors. Second 37 and fourth 39 carriers are received at the grips 21 of the deviators 33, 34. When detectors 41 indicate that release position or positions is/are free, deviators may turn towards the indicated free position. In this sequence the second 37 and fourth 39 carriers are transferred to adjacent conveyor. Operating position in FIG. 15 shows a starting position wherein two more carriers have entered the deviators for continuing the operation.

Figure 17:
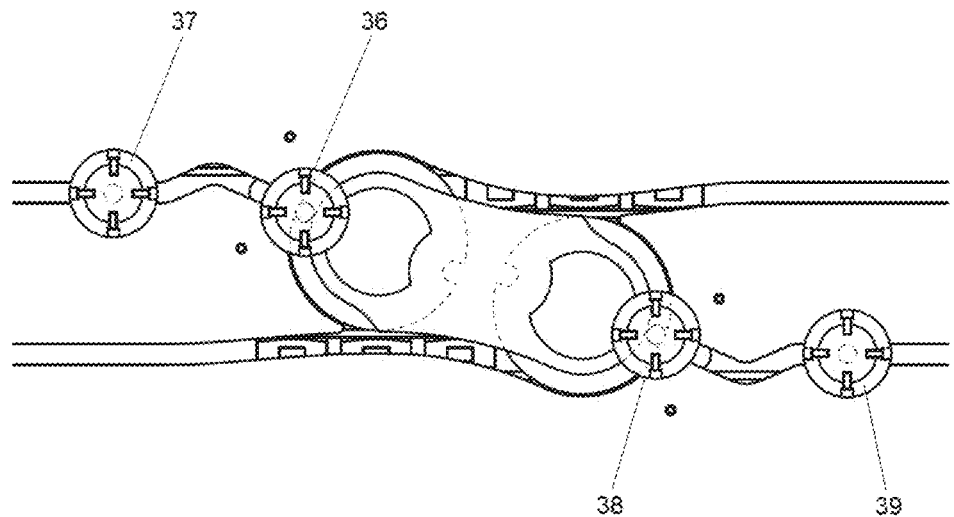
Figure 18:
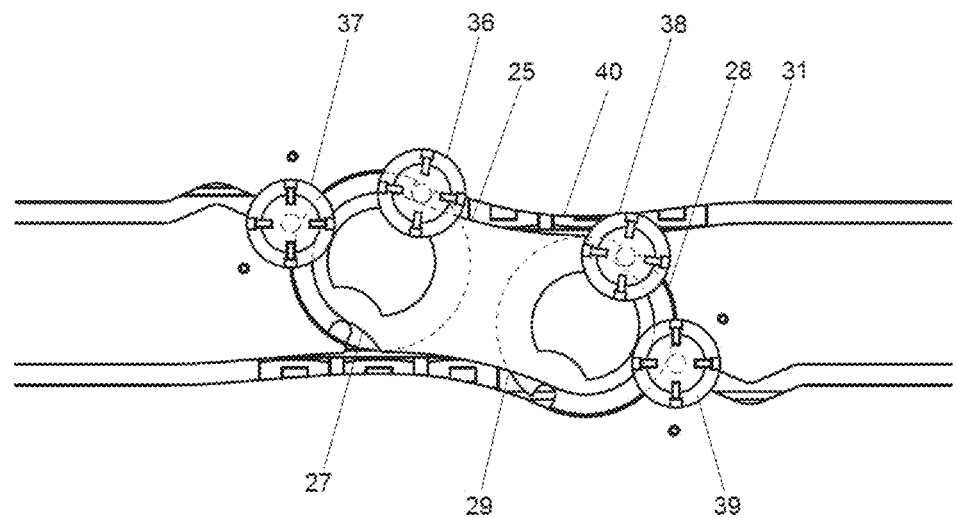
Figure 19:
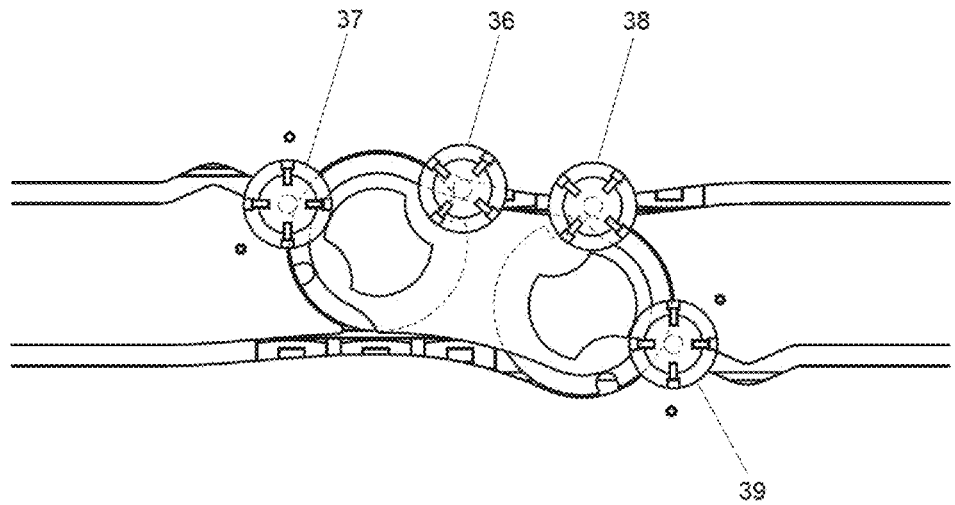
Figure 20:
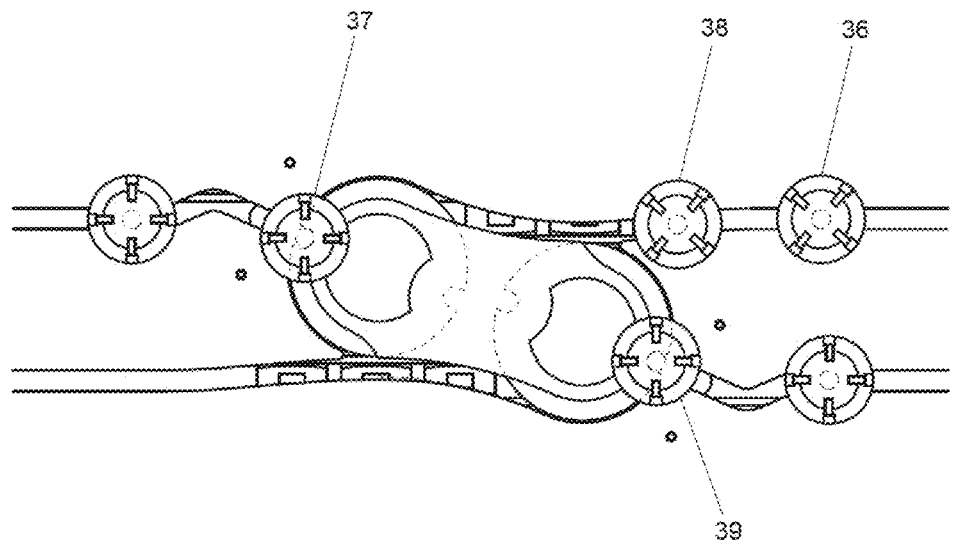
Figure 21:
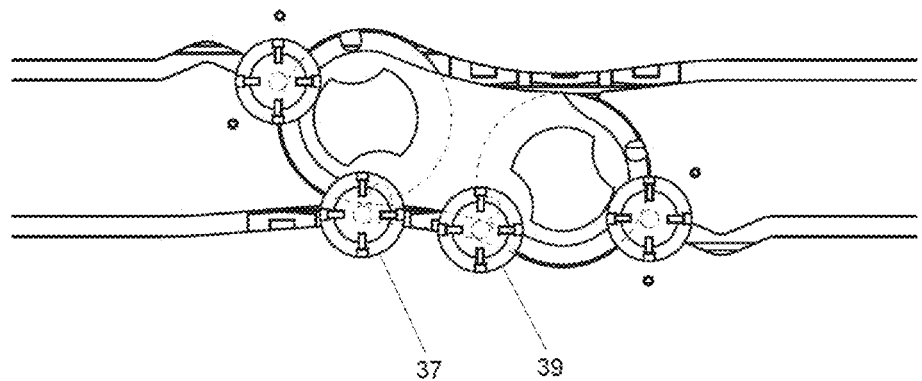
Figure 22:
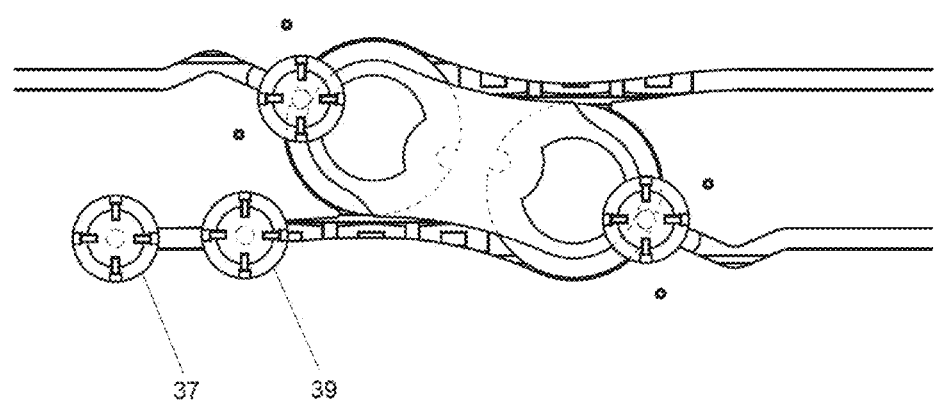

FIGS. 16 to 22 show an alternative sequence for transferring two carriers 36, 38 or 37, 39 from two different conveyors by two deviators 33, 34 to one conveyor. The sequence starts (FIG. 16) by receiving a carrier 36, 38 to each deviator 33, 34. In FIG. 17 the carriers have been received on grips 21 of the deviators 33, 34 and second and fourth carriers 37, 39 are travelling to deviators 33, 34. Next, the deviators 33, 34 are turned towards the exit side 31 of the straight conveyor. As can be seen from FIG. 18, the first deviator 33 must stop before releasing the first carrier 36 on the conveyor. The deviator is stopped at the beginning of the pushing surface 25. The second deviator is now rotated so that its grip 21 is at the beginning of a second pushing surface 28. Now the second deviator can be rotated to release the third carrier 38 and as soon as detectors 40 indicate that the third carrier has been released, the first deviator can be released in order to feed the first carrier 36 to the conveyor. The release position is shown in FIG. 19. FIGS. 20-22 show the same sequence for transferring carriers to the conveyor on the opposite side of the deviator pair.

Thus, while there have been shown and described and pointed out fundamental novel features of the invention as applied to a preferred embodiment thereof, it will be understood that various omissions and substitutions and changes in the form and details of the method and device may be made by those skilled in the art without departing from the spirit of the invention. For example, it is expressly intended that all combinations of those elements and/or method steps which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

REFERENCE SIGNS LIST 1 carrier
2 transportation module
3 base plate
4 conveyor
5 guide wheel
6 belt
7 guide block
8 drive motor
9 guide plate
10 groove
11 glide plate
12 neck part
13 meshing plate
14 detection surface
15 holder
16 deviator
17 deviator, four grips
18 stem
19 deviator motor
20 deviator plate
21 grip
22 contact surface
23 bumper plate
24 push plate
25 pushing surface
26 incoming zone
27-29 pushing surfaces
30 incoming side of a straight conveyor
31 exit side of a straight conveyor
32 convoluting conveyor
33 first deviator
34 second deviator
35 photodetector
36-39 test tube carriers
40 detector
41 RFID reader

The invention claimed is:

1. An arrangement for sequencing and guiding travel of test tube carriers transported on at least one conveyor, the arrangement comprising:
    at least one conveyor,
    one rotatable deviator positioned to intersect the at least one conveyor, the deviator comprising a horizontal deviator plate including at least one grip for receiving a test tube carrier, and
    at least one push plate positioned in proximity of the deviator plate and having two pushing surfaces formed as arcs that start as tangents of a circle defined by tracks that a bottom of a recess of the grip travels and then curve outwards from said circle.

2. The arrangement according to the claim 1, further comprising:
    at least two deviators having horizontal deviator plates having four pushing surfaces formed as an arc that starts as a tangent of a circle defined by the track that the bottom of the recess of the grip travels and then curves outwards from said circle,
wherein the at least one push plate is positioned in proximity of the horizontal deviator plates of the at least two deviators.

3. The arrangement according to claim 1, further comprising at least one contact surface positioned vertically at a distance from the deviator plate and aligned with the grip, the contact surface being formed to contact the test tube carrier at a distance from the contact level of the grip and the carrier.

4. The arrangement according to claim 1, wherein the grip is a recess on a circular plate.

5. The arrangement according to claim 3, wherein the contact surface is a recess on a circular plate.

6. The arrangement according to claim 3, wherein the grip and the contact surface are formed as a part of an arc of a circle.

7. The arrangement according to claim 3, wherein at least one deviator comprises at least four grips and contact surfaces.

8. The arrangement according to claim 1, further comprising at least two deviators arranged to both intersect two conveyors.

9. The arrangement according to claim 1, further comprising at least one test tube carrier comprising a circular glide plate having a diameter and a thickness, a neck part on top of the glide plate having a diameter smaller than the glide plate and a length, a meshing plate having a diameter and a thickness and being placed at a distance from the glide plate.

10. The arrangement according to claim 9, wherein the glide plate comprises a RFID chip and the diameter of the neck part is smaller than the largest dimension of the chip.

11. The arrangement according to claim 10, wherein the carrier comprises a detection surface positioned between the neck part and the meshing plate, the detection surface having a diameter smaller than the diameter of the meshing plate and a thickness, the diameter of the detection surface being larger than the diameter of the neck part.

12. The arrangement according to claim 11, wherein the carrier comprises a detection surface positioned on the opposite side of the meshing plate in relation to the neck part, the detection surface having a diameter smaller than the diameter of the meshing plate and a thickness, the diameter being larger than the diameter of the neck part.

13. The arrangement according to claim 10, wherein the glide plate comprises a seat for a RFID chip to which the chip can be installed from the bottom surface of the glide plate opposite to the neck part so that the chip can be read from the bottom of the carrier formed by the bottom surface of the glide plate.

14. The arrangement according to claim 1, wherein the pushing surface follows the circle.

15. The arrangement according to claim 1, wherein the deviator is configured to rotate in either a clockwise or counter-clockwise direction.

16. The arrangement according to claim 1, wherein the pushing surfaces are located on opposing sides of the circle.

17. A method for sequencing and guiding travel of test tube carriers transported on at least one conveyor, comprising:
receiving at least one test tube carrier on one rotatable deviator positioned to intersect the at least one conveyor by at least one grip formed on a horizontal deviator plate for receiving the test tube carrier,
rotating the at least one test tube carrier by the deviator, and
pushing said at least one test tube carrier from the deviator by at least one push plate positioned in proximity of the deviator plate and having two pushing surfaces formed as arcs that starts as tangents of a circle defined by tracks that a bottom of a recess of grip travels and then curve outwards from said circle.

18. The method according to claim 17, further comprising supporting said test tube carrier against tilting by at least one contact surface positioned vertically at a distance from the deviator plate and aligned with the grip, the contact surface being formed to contact said test tube carrier at a distance from the contact level of the grip and said carrier so that said carrier contacts the surface of said grip and said contact surface simultaneously when said carrier enters said deviator.

19. The method according to claim 18, further comprising transporting at least one test tube carrier comprising a circular glide plate having a diameter and a thickness, a neck part on top of the glide plate having a length and a diameter smaller than the glide plate, and a meshing plate having a diameter and a thickness and being placed at a distance from the glide plate, wherein the glide plate comprises a RFID chip and the diameter of the neck part is smaller than the largest dimension of the chip.

* * * * *